US 7,525,654 B2

(12) United States Patent
Drennen, III et al.

(10) Patent No.: US 7,525,654 B2
(45) Date of Patent: Apr. 28, 2009

(54) TUNABLE LASER-BASED CHEMICAL IMAGING SYSTEM

(75) Inventors: James K. Drennen, III, Mars, PA (US); Carl A. Anderson, Cranberry Township, PA (US); Robert P. Cogdill, Pittsburgh, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 11 days.

(21) Appl. No.: 10/969,424

(22) Filed: Oct. 20, 2004

(65) Prior Publication Data

US 2006/0082777 A1    Apr. 20, 2006

(51) Int. Cl.
*G01J 3/42*    (2006.01)

(52) U.S. Cl. .................. 356/320; 250/205; 250/339.02; 250/339.07

(58) Field of Classification Search ................ 356/300, 356/301, 446, 432; 250/339.01, 339.02, 250/339.07
See application file for complete search history.

(56) References Cited

U.S. PATENT DOCUMENTS

| | | | |
|---|---|---|---|
| 4,176,963 A * | 12/1979 | Fabinski et al. | 356/418 |
| 5,048,959 A | 9/1991 | Morris et al. | |
| 5,216,484 A | 6/1993 | Chao et al. | |
| 5,339,151 A * | 8/1994 | Shinn | 356/328 |
| 5,533,139 A * | 7/1996 | Parker et al. | 382/108 |
| 5,777,736 A | 7/1998 | Horton | |
| 5,838,435 A | 11/1998 | Sandison | |
| 5,859,700 A | 1/1999 | Yang | |
| 6,002,476 A | 12/1999 | Treado | |
| RE36,529 E | 1/2000 | Lewis et al. | |
| 6,100,974 A | 8/2000 | Reininger | |
| 6,337,472 B1 | 1/2002 | Garner et al. | |
| 6,373,568 B1 | 4/2002 | Miller et al. | |
| 6,483,112 B1 | 11/2002 | Lewis | |
| 6,640,130 B1 | 10/2003 | Freeman et al. | |
| 6,690,464 B1 | 2/2004 | Lewis et al. | |
| 6,690,466 B2 | 2/2004 | Miller et al. | |
| 2001/0052979 A1 | 12/2001 | Treado et al. | |
| 2002/0113210 A1 * | 8/2002 | Treado et al. | 250/331 |
| 2003/0004419 A1 | 1/2003 | Treado et al. | |
| 2003/0018272 A1 | 1/2003 | Treado et al. | |
| 2004/0159789 A1 | 8/2004 | Treado et al. | |
| 2004/0184660 A1 | 9/2004 | Treado et al. | |
| 2005/0213089 A1 | 9/2005 | Margalith et al. | |

OTHER PUBLICATIONS

Kacey Claborn, Eileen Puklin-Faucher, Miki Kurimoto, Werner Kaminsky, and Bart Kahr; "Circular Dichroism Imaging Microscopy: Application to Enantiomorphous Twinning in Biaxial Crystals of 1,8-Dihydroxyanthraquinone"; JACS Articles Published on Web Nov. 8, 2003; J. Am. Chem. Soc. vol. 125, No. 48 2003; pp. 14825-14831.

* cited by examiner

*Primary Examiner*—Gregory J Toatley, Jr.
*Assistant Examiner*—Juan D Valentin
(74) *Attorney, Agent, or Firm*—Buchanan Ingersoll & Rooney PC; Craig G. Cochenour

(57) ABSTRACT

A chemical imaging device which utilizes a computer controlled tunable laser to provide light of wavelengths in the near infrared band and a focal plane array to image a sample illuminated at various wavelengths of light. The device also provides light intensity reference detectors at the source and terminus of the light delivery pathway for normalizing the collected images and for detecting defects in the light delivery pathway.

27 Claims, 3 Drawing Sheets

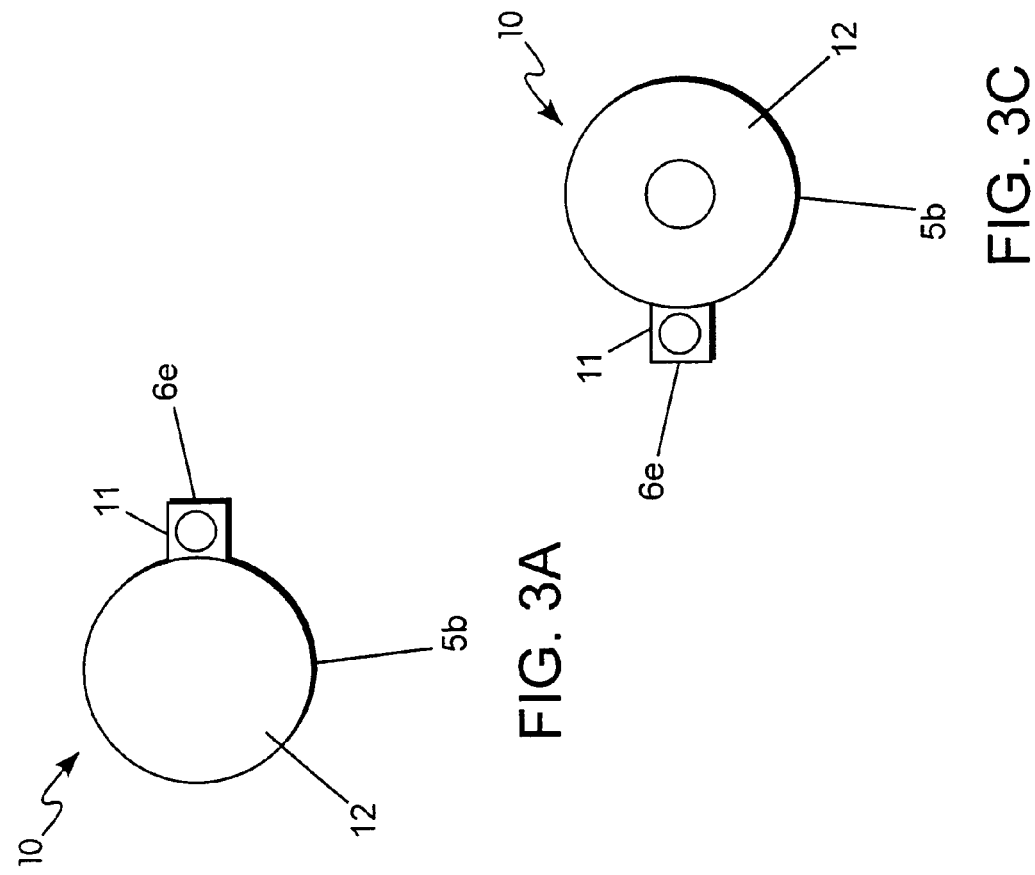

TUNABLE LASER-BASED CHEMICAL IMAGING SYSTEM

FIELD OF THE INVENTION

This invention relates to the field of chemical imaging of samples, and, in particular, to chemical imaging of samples illuminated by light in the near-infrared range.

BACKGROUND OF THE INVENTION

Chemical imaging is a well-known method for obtaining information about the molecular makeup of a particular material that combines digital imaging and near-infrared (NIR) spectroscopy. By illuminating the material with light of a particular wavelength, or with a broadband illumination source, and observing the light reflected or transmitted by the material at various wavelengths, it is possible to determine the composition of the material, as is well known in the art. By utilizing digital imagery in combination with NIR spectroscopy, it is possible to obtain two or three dimensional data structures which can be converted into chemical images of the surface of the sample.

The chemical imaging method includes delivering narrow band or broadband radiation to a sample and collecting the radiation that is either reflected from or transmitted through the sample via a focal plane array, a camera or raster scanned detector to yield a spectral image by modulating either the wavelength of the illumination source or the center wavelength of interference filters placed between the sample and the image detector. A complete spectral image hypercube of a sample is thus acquired in steps, wherein each pixel of the hypercube contains the optical intensity spectrum across the sample wavelength range for a specific X-Y position.

Prior art chemical imaging methods and apparatus consisted of taking point-by-point spectra of a small region of the surface of a sample and rasterizing the spectra to obtain the chemical image. This method is time-consuming and cumbersome, in that many point spectra must be collected to make a chemical image of desirable resolution.

Alternatively, chemical images may be collected using a CCD or focal plane array to collect the image over the entire desired area. Such a system is described in U.S. Pat. No. 6,734,932 (Treado, et al.), entitled "Near Infrared Chemical Imaging Microscope". The Treado imager is an interferometric type imager which utilizes a broadband NIR or white-light illumination source, a tunable filter, such as a liquid crystal tunable filter (LCTF) or an acousto-optic tunable filter (AOTF) for wavelength discrimination, and a CCD or FPA for image capture. This type of imager, however, suffers from several drawbacks. First, broadband source illumination and inefficient light collection can have an adverse impact on the signal-to-noise ratio of the imager. Constant, broadband illumination can also often be damaging to labile samples, for example, biological specimens, thereby limiting the application of the device. Interferometric-type imagers are also limited in their ability to operate in alternative modes. For example, it is difficult to perform Stokes vibrational circular dichroism (VCD) spectroscopy, with an interferometric-type imager because the signal-to-noise ratio (SNR), optical geometry, and acquisition speed are prohibitive. Lastly, the collection of reference images for the normalization of collected chemical images can be time-consuming and cumbersome, requiring the collection of a reference image at the tunable filter for each wavelength interval of interest.

Tuned illumination type imagers are also known in the art. These type of imagers function by illuminating the samples with light of a single wavelength or a weighted combination of multiple spectral bands. Detection using these types of imagers is simplified because the need for the interferometric element (i.e., the tunable filter) is eliminated. Beam delivery is also simplified by the use of fiber optic and hollow waveguide technology. Current, prior art tuned illumination imagers utilize grating monochromaters, LEDs or laser diodes to provide single or very narrow-band wavelength illumination. Such a device is disclosed in U.S. Pat. No. 6,690,466 (Miller, et al.), entitled "Spectral Imaging System," in which the tuned illumination source consists of an array of LEDs, with one LED per spectral channel.

SUMMARY OF THE INVENTION

The chemical imaging apparatus of the present invention is a tunable illumination type imager which utilizes an actively tuned source illumination, in this case, a tunable near infrared laser. The use of the tunable laser in this context is novel in the art and represents an improvement over current prior art tunable illumination devices, many of which utilize discrete LEDs or laser diodes for illumination. Further improvements over the current state of the prior art include the use of one or more reference detectors in the illumination delivery path, which obviates the need for the collection of reference samples at the point of illumination. Reference detectors are also useful for providing a self-diagnostic function to detect defects in the optical pathway between the source of illumination and the point of illumination of the sample. The device is also easily configurable to operate in either reflectance or transmission modes and can be easily retrofitted with optical filters and polarizers for use in Raman, laser induced fluorescence and polarimetry measurements.

BRIEF DESCRIPTION OF THE DRAWINGS

FIGS. 3a, 3b, and 3c provides back, side, and front views respectively of the fiber terminus having an integrated detector therewith.

DETAILED DESCRIPTION OF THE INVENTION

Figure 1:
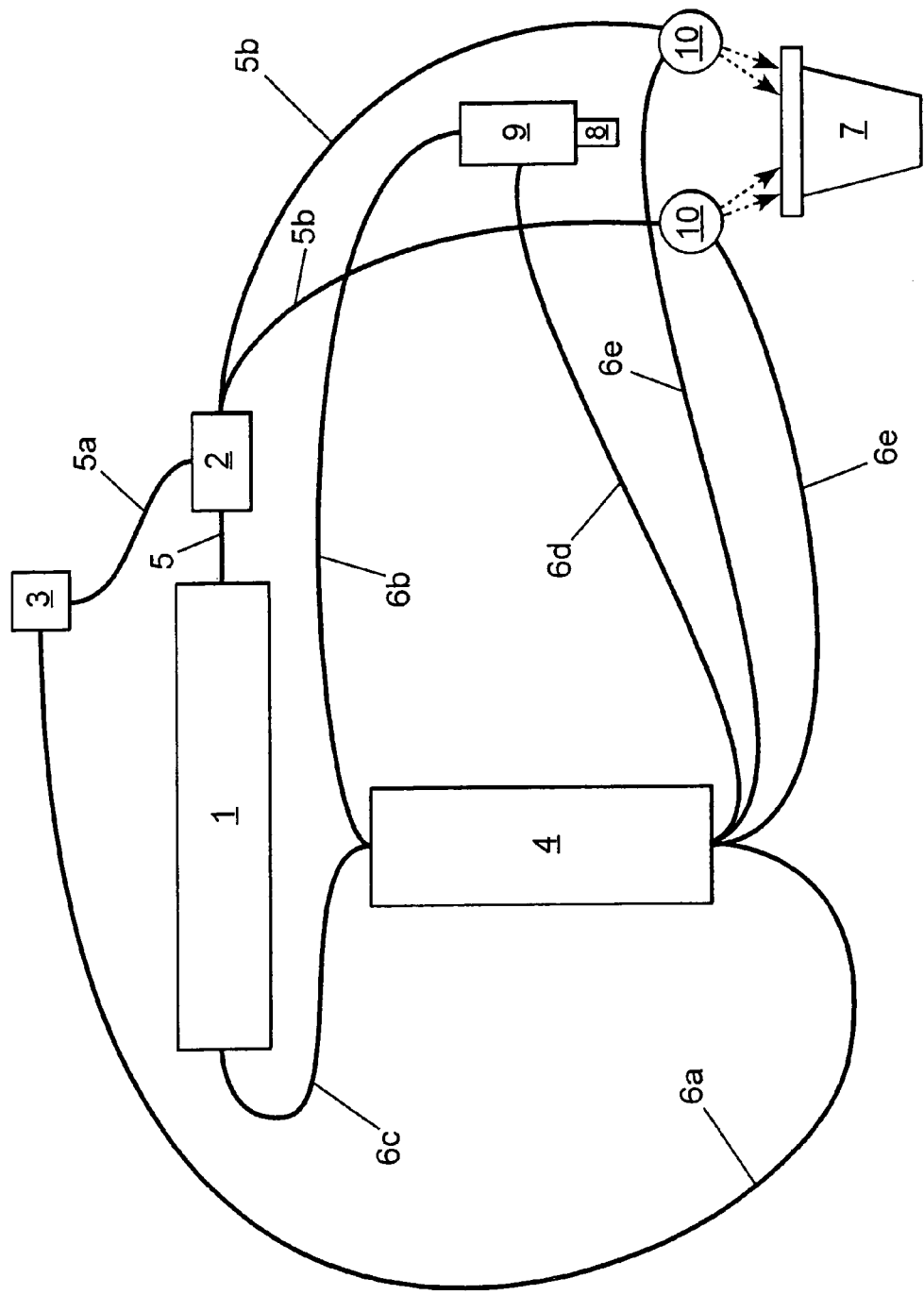
FIG. 1 is a schematic representation of the imaging apparatus of the present invention configured for performing reflectance imaging.

The preferred embodiment of the invention is shown in schematic representation in FIG. 1. Reference No. 1 is a tunable illumination source, preferably a near infrared (wavelengths approximately 700 to 2500 nm) tunable laser of a type such as that made by Opotek Corporation of Carlsbad, Calif. In an alternate embodiment, the tunable laser can be replaced with a tunable illumination source capable of providing illumination over a broader range of wavelengths, including visible and ultraviolet illumination. Preferably, the tunable laser is able to be tuned to individual wavelengths with a resolution of 10 cm$^{-1}$, with a tuning resolution that is adjustable depending on the analytical need, and is not less than 5 cm$^{-1}$. Preferably, tunable laser 1 can be tuned via a computer controlled interface.

Fiber optic cable 5 delivers the output of tunable laser 1 to a beam splitter 2. Beam splitter 2 is preferably a polarizing beam splitter of the type sold by Control Optics of Ontario, Canada. The tuned illumination generated by tunable laser 1 is split at beam splitter 2, with one leg of the split being delivered via fiber optic cable 5a to reference detector 3, and the other leg of the split being delivered to fiber terminus 10 through fiber optic cable 5b. In reflectance mode, where illumination from multiple sources is desired to reduce shadow effects, multiple beam splitters may be necessary. Therefore, in the schematic representation shown in FIG. 1, beam splitter 2 would, in reality, consist of two discrete physical beam splitters.

The details of fiber terminus 10 with integrated detector 11 are shown in FIGS. 3a 3b, and 3c, showing fiber terminus 10 in back, side, and front views, respectively. Fiber terminus 10 consists of integrating sphere 12, preferably of the typemodel IS-010sold by Pro-Lite Technology of the United Kingdom. Integrating sphere 12 serves to provide a highly uniform illumination pattern across the surface of the sample. Fiber terminus 10 also includes integrated detector 11. Integrated detector 11 is a simple photovoltaic detector, preferably a mercury cadmium telluride (MCT) photovoltaic detector, and may include an analog-to-digital converter (ADC) for converting analog illumination intensity information into digital form, which may be returned to computer 4 via cable 6e.

Figure 2:
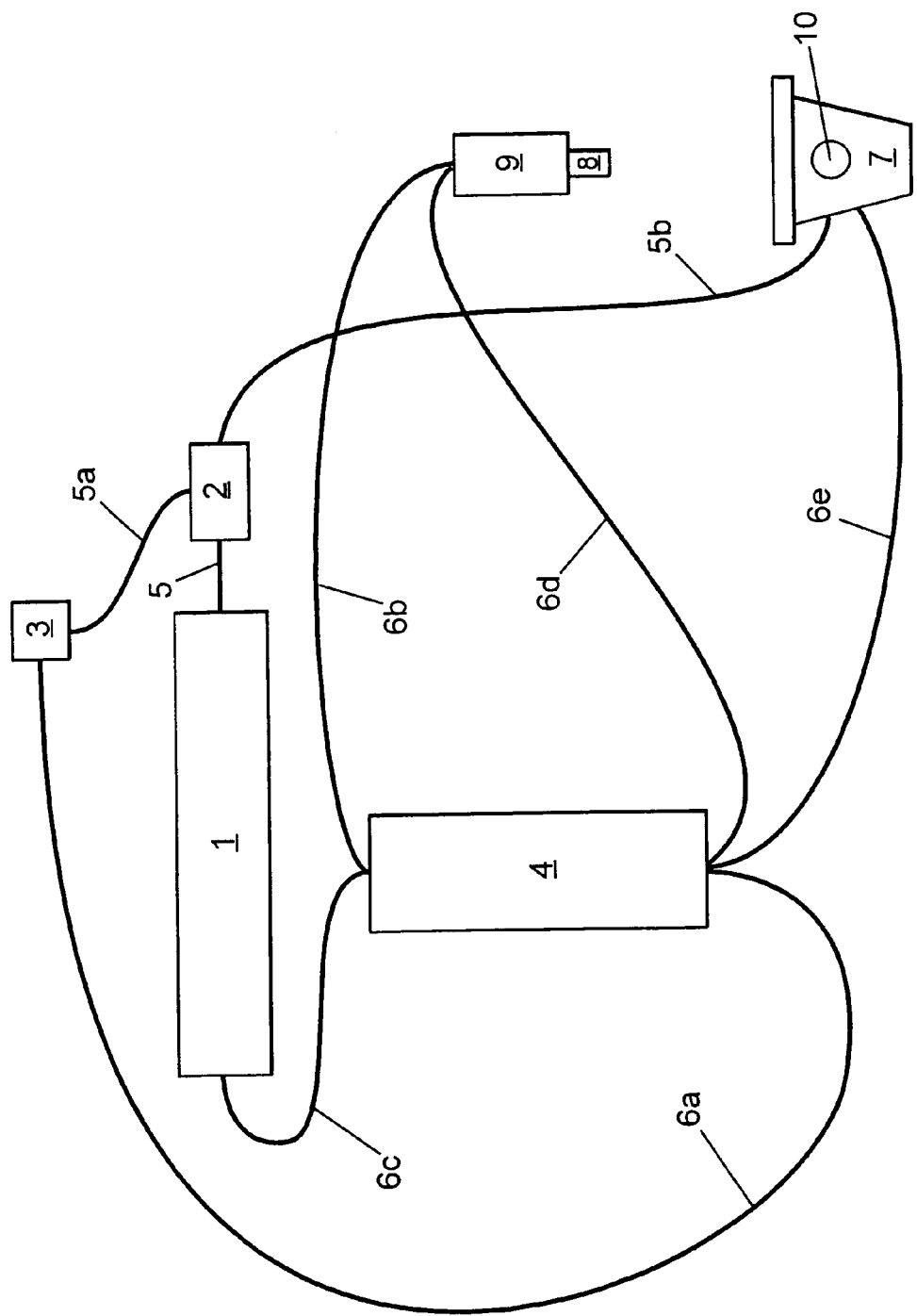
FIG. 2 is a schematic representation of the imaging apparatus of the present invention configured for transmission imaging.

The device can be configured to operate in reflectance mode, as shown in FIG. 1, or in transmission mode, as shown in FIG. 2. In the reflectance configuration shown in FIG. 1, multiple fiber terminals 10 are shown to provide general all around illumination and to eliminate or limit shadow effects with respect to a sample, which is positioned on stage 7. Camera 9 is configured to collect light which is reflected from the sample. In transmission configuration, shown in FIG. 2, a single fiber terminus 10 is utilized and is positioned under stage 7 such that the light emitted therefrom will be transmitted through the sample to camera 9, positioned above the sample, to collect light which is transmitted through the sample.

Camera 9 is preferably a near infrared (NIR) camera utilizing an MCT based focal plane array sensor, but any camera capable of digitizing an image in the NIR wavelength range can be used. Camera 9 is fitted with objective 8, which is preferably an achromatic lens or wavefront coded lens. Other optical elements may also be used in conjunction with camera objective 8, including optical filters and polarizers (not shown) for use in various alternative types of imaging, including VCD, Raman, and laser induced fluorescence.

Computer 4 is a standard personal type computer which provides control of all components of the imager. Computer 4 is able to control the wavelength at which tunable illumination source 1 emits light via cable 6c. In addition, computer 4 is able to control infrared camera 9 via control cable 6b. Digital image data collected by camera 9 is returned to computer 4 via cable 6d for formatting and storage.

The other function of computer 4 is to provide normalization of the collected data and error detection for the overall process. Reference detector 3 is preferably an MCT photovoltaic detector capable of detecting the intensity of the tuned illumination delivered via fiber optic cable 5a. Analog-to-digital conversion (ADC) and temperature controls are co-located with the reference detectors to prevent signal contamination from external electromagnetic noise sources. The digital information is sent via data cable 6a to computer 4 and image data collected from camera 9 via cable 6d is normalized by computer 4 with respect to the intensity of the illuminating light as provided by reference detector 3. Mathematically, the measured intensity at each pixel will be divided by value of the illumination at reference detector 3 for the wavelength of light being measured. In this fashion, each plane (wavelength) of data within the spectral hypercube will be normalized to the reference value. This is a novel feature which provides real time collection of reference values, eliminating the need to collect individual reference images by imaging a reference sample at each wavelength. Reference detectors 11, located at fiber terminals 10 may also be used for this function. When using reference detectors 11 for this purpose, the measured intensity at each pixel will be divided by the mean of the output of the multiple fiber terminus reference detectors 11 for the wavelength of light being measured. As such, each plane of data within the spectral hypercube will be normalized to the intensity of the light measured at fiber terminus reference detectors 11. This feature alone provides a significant reduction in the time necessary to perform the chemical imaging over known prior art systems.

Reference detectors 11 may also be used as a self-diagnosis tool to detect defects or changes in the optical path. Reference detectors 11 collect information regarding the intensity of the beam which is delivered to the sample and it is compared to the intensity of the beam collected by reference detector 3 by computer 4 to ensure that degradation of the light source between splitter 2 and fiber terminus 10 has not occurred. Ideally, the relative intensity ratio of the light at fiber terminus 10 to the light at reference detector 3 should remain constant.

The imager of the present invention is also capable of self correcting for noise induced in the collected spectrum by operating inefficiencies inherent in the components. To do this, an image is collected absent illumination, and the "dark" image is subsequently subtracted from images collected under illumination. The "dark" noise is subtracted from reference detectors 10 and 3 in a similar fashion. Noise can therefore be detected with pixel-level resolution and automatic compensation applied, such that a normalized image corrected for induced noise could be calculated on a pixel-by-pixel basis using the general formula $(P_{sample\ image} - P_{dark\ image})$/(reference value−dark reference value).

Fiber optic cables 5, 5a and 5b may be replaced with hollow waveguides of a type well known in the art, to provide a more efficient delivery of light from tunable laser 1 to fiber terminus 10.

In operation, computer 4 cycles tunable illumination source 1 through a range of wavelengths. A sample, located on stage 7, is illuminated through one or more fiber terminals 10 by the tuned illumination. Data is collected via camera 9 and sent to personal computer 4 for normalization with respect to the illumination reference value detected by reference detector 3 or reference detector(s) 11. Thus, the images collected at each wavelength, when combined, provide a complete spectral image hypercube of the sample wherein each pixel of the hypercube contains the optical intensity spectrum across the sampled wavelength range for a particular spatial position.

We Claim:
1. A chemical imaging system comprising:
a tunable light source;
a light delivery medium for delivering light of a specific tuned wavelength from said tunable light source to a sample ,wherein said light delivery medium ends in one or more terminals for illuminating said sample;
one or more reference detectors for detecting the intensity ratio of said tuned light at said tunable light source and at one or more points along said light delivery medium and at said one or more terminals of said light delivery medium;
a detector, for detecting light reflected from or transmitted through said sample;
a controller for tuning said tunable light source in a predetermined pattern; and a data collection device for collecting and storing information from said detector, wherein said controller and said data collection device normalize said stored information with respect to any combination of reference value readings from said one or more reference detectors, and provide light source intensity normalization such that each plane or wavelength of data within a spectral hypercube is normalized to the reference value.

2. The chemical imaging system of claim 1 wherein said tunable light source is a laser capable of being tuned to generate light of a specific wavelength.

3. The chemical imaging system of claim 2 wherein said specific wavelength is within the near infrared band.

4. The chemical imaging system of claim 2 wherein said specific wavelength is within a band selected from a group consisting of infrared, near infrared, visible and ultraviolet.

5. The chemical imaging system of claim 2 wherein said light delivery medium is selected from a group consisting of fiber optics cables and hollow wave guides.

6. The chemical imaging system of claim 5 wherein said detector is a camera.

7. The chemical imaging system of claim 6 wherein said camera is capable of capturing images in the near infrared.

8. The chemical imaging system of claim 7 wherein said camera utilizes a focal plane array.

9. The chemical imaging system of claim 6 wherein said one or more terminals of said light delivery medium illuminates said sample with a uniform pattern of light.

10. The chemical imaging system of claim 9 wherein said terminal is an intergrating sphere.

11. The chemical imaging system of claim 9 wherein said light delivery medium comprises:

one or more beam splitters coupled to said tuned light source; and two or more discrete pathways coupled to said splitter for the delivery of tuned light from said splitter to two or more terminals.

12. The chemical imaging system of claim 11 wherein said one or more reference detectors include a source reference detector configured to detect the intensity of tuned light as it leaves said tuned light source.

13. The chemical imaging system of claim 12 wherein said source reference detector is coupled to said light delivery element via a beam splitter.

14. The chemical imaging system of claim 11 wherein said one or more reference detectors includes a terminus reference detector coupled to each of said terminals to measure the intensity of light at each of said terminals.

15. The chemical imaging system of claim 1 wherein said controller and said data collection device is a computer.

16. The chemical imaging system of claim 12 wherein said controller and said data collection device is a computer.

17. The chemical imaging system of claim 16 wherein said computer is coupled to said tunable light source and is capable of instructing said tunable light source to tune its output to a given discrete wavelength within a predefined band of wavelengths.

18. The chemical imaging system of claim 17 wherein said computer is capable of sequencing said tunable light source through a predefined series of wavelengths.

19. The chemical imaging system of claim 17 wherein said computer is coupled to said camera and is capable of capturing images from said camera and storing said images on a storage medium.

20. The chemical imaging system of claim 19 wherein said computer is coupled to said one or more reference detectors and is capable of receiving a reading from each of said one or more reference detectors representing the intensity of said tuned light at each of said detectors.

21. The chemical imaging system of claim 20 wherein said computer is capable of normalizing said stored image collected from said camera with respect to any combination of readings from said one or more reference detectors.

22. The chemical imaging system of claim 21 wherein said computer is capable of detecting noise generated by other components in the system and correcting said stored images to eliminate the effect of said noise.

23. The chemical imaging system of claim 22 wherein said noise is detected by collecting image data absent any illumination and subtracting the collected image from images collected for each wavelength use to illuminate said sample.

24. A chemical imaging system comprising:

a near infrared tunable laser;

a light delivery medium for delivering one or more pathways of light from said tunable laser to a sample, wherein said light delivery medium ends in one or more terminals;

one or more reference detectors for detecting the intensity ratio of said tuned light at said tunable light source and at one or more points along said light delivery medium and at said one or more terminals of said light delivery medium;

a camera for capturing images, including said images in the near infrared band, of light reflected from or transmitted through said sample; and a computer, coupled to said tunable laser for controlling the wavelength of light output by said laser and coupled to said camera, for capturing and storing said images captured by said camera, wherein said computer normalizes said stored images with respect to any combination of reference value readings from one or more of said reference detectors, and provides source intensity normalization such that each plane or wavelength of data within a spectral hypercube is normalized to the reference value.

25. The chemical imaging system of claim 24 further comprising one or more reference detectors located at various points along said light delivery medium for collecting information regarding the intensity of light at said various points, said reference detectors are coupled to said computer and communicate said intensity information to said computer.

26. The chemical imaging system of claim 25 further comprising one or more beam splitters for splitting said light delivery medium into multiple pathways or for attaching said reference detectors at said various points.

27. The chemical imaging system of claim 24 wherein said camera utilizes a sensing element select from a group consisting of a charge coupled device and a focal plane array.

* * * * *